(12) United States Patent  (10) Patent No.: US 6,569,171 B2
DeGuillebon et al.  (45) Date of Patent: May 27, 2003

(54) SAFETY LOCKING MECHANISM FOR A MEDICAL CLIP DEVICE

(75) Inventors: Henri F. DeGuillebon, Manchester/Sea, MA (US); Emmanuel Manetakis, Burlington, MA (US)

(73) Assignee: Microline, Inc., Beverly, MA (US)

( * ) Notice: Subject to any disclaimer, the term of this patent is extended or adjusted under 35 U.S.C. 154(b) by 18 days.

(21) Appl. No.: 09/934,378

(22) Filed: Aug. 21, 2001

(65) Prior Publication Data

US 2002/0120279 A1 Aug. 29, 2002

Related U.S. Application Data

(63) Continuation-in-part of application No. 09/795,808, filed on Feb. 28, 2001.

(51) Int. Cl.[7] .............................................. A61B 17/10
(52) U.S. Cl. .................... 606/142; 606/139; 606/143
(58) Field of Search .................... 606/139, 142, 606/143, 219, 221; 227/175.1, 175.4, 175.2, 175.3

(56) References Cited

U.S. PATENT DOCUMENTS 4,892,244 A * 1/1990 Fox et al. ................. 227/175.4
5,607,436 A * 3/1997 Pratt et al. .................. 606/143

* cited by examiner

*Primary Examiner*—Julian W. Woo
(74) *Attorney, Agent, or Firm*—Don Halgren

(57) ABSTRACT

An elongated medical clip applying device having a hand holdable housing at a proximal end thereof and a barrel clip-dispenser at a distal end thereof is arranged for dispensing squeezable clips onto a mammalian tissue. The device includes a hollow inner sleeve arranged within the housing. The sleeve has a proximal end for receiving a clip feeder cartridge therein. A proximal bearing is slidably disposed about a proximal circumference of the inner sleeve. A trigger lever is attached to the housing, the trigger lever having a linkage bar thereon connected to a finger for moving the proximal bearing proximally and distally. A lock mechanism is arranged in the sleeve to deny a clip feeder cartridge entry into the sleeve when the proximal bearing is adjacent the lock mechanism.

14 Claims, 4 Drawing Sheets

SAFETY LOCKING MECHANISM FOR A MEDICAL CLIP DEVICE

This is a continuation-in-part of U.S. application Ser. No. 09/795,808, filed on Feb. 28, 2001.

BACKGROUND OF THE INVENTION

1. Field of the Invention

This invention relates to devices for applying clips to mammalian vessels and tissue and more particularly to a safety locking mechanism for such a clip applying device.

2. Prior Art

Modem surgery may be identified as laparoscopic surgery, which may be defined as minimally invasive surgery upon a patient, utilizing small or miniaturized medical devices by which body tissue is cut, removed or cauterized by small manipulable devices through small incisions or openings within the patient's body. A grasper or dissector is one such tool for that type of surgery. Such a device may be utilized to grab, dissect, treat or move tissue out of the surgical situs where other tissue may be surgically treated.

There is a need for a readily manipulable device for the grasping and or crimping/sealing of tissue by the single hand of an operating surgeon.

It is an object of the present invention to provide a grasper, dissector or crimper which is an improvement over the prior art.

It is a further object of the present invention to provide a safety mechanism for such a grasper or crimper to control the loading of such a device.

It is another object of the present invention to prevent problems of loose clips or a loose cartridge.

It is another object of the present invention to provide a grasper, dissector or crimper which will not be overloaded and wherein jamming of its jaws and its clips will be prevented.

It is yet another object of the present invention to provide a simple clip feed through mechanism with a safety lock which overcomes and helps avoid the problems of the prior art.

BRIEF SUMMARY OF THE INVENTION

The present invention relates to a clip applying apparatus utilized in medical procedures for pinching off and clinching together mammalian tissue. Such a clip applying device comprises a pistol shaped housing at a proximal end thereof, with an elongated barrel extending therefrom, the barrel having a distal end from which extends a pair of pincher jaws. The pistol-shaped housing has a bore extending therethrough for receipt of an inner sleeve. The inner sleeve extends through the housing and itself receives a clip loaded cartridge from its proximalmost end.

The housing has a fixed handle portion extending downwardly therefrom, and a trigger lever which is pivotably disposed in the housing and swings about an axis therebetween. An elongated ratchet plate is fixedly attached to the trigger lever. The elongated ratchet plate has a distal end with a plurality of ratchet teeth formed thereon. A bifurcated finger is fixedly attached to an upper end of the trigger lever, and is disposed within the housing about opposite sides of the inner sleeve. The bifurcated finger is disposed about a cylindrical portion of a distal bearing which slides forwardly and rearwardly about the inner sleeve. The distal bearing is connected via an elongated shaft to a housing to squeeze the pincher jaws closed.

An elongated lever interface arm has a lower end which is pivotably attached to the fixed handle of the housing at a midpoint thereof. The elongated lever interface arm has a distal end comprised of a second bifurcated finger arrangement which is disposed about opposite sides of a proximal bearing. The proximal bearing is disposed on the proximal end of the inner sleeve within the pistol shaped housing.

An elongated linkage bar is pivotably attached at a first end thereof, to the elongated ratchet plate. The linkage bar has an elongated slot disposed therein in an axial arrangement near its second or distal end. A pivot pin extends through a pivot hole in the elongated lever interface arm and into the axially directed slot near the distal end of the linkage bar. A coiled spring is arranged between the lowermost end of the fixed handle and an extension arranged on the upper end of the elongated ratchet plate. The coiled spring provides a biasing force against which the trigger lever must be pulled.

A ratchet pawl is arranged around the pivot axis on the lowermost or proximal end of the elongated lever interface arm. The ratchet pawl is arranged to engage the ratchet teeth on the distal end of the elongated ratchet plate.

The inner sleeve arranged within the bore of the pistol shaped housing, has an elongated slot arranged in an axially disposed orientation at a midpoint thereof An elongated lock key is pivotably disposed within the inner sleeve in the housing, about a key pivot axis, which axis is fixed within the inner sleeve cylinder. The pivotable lock key has an enlarged distalmost end which is arranged to pivot into and out of the bore of the inner sleeve, and within the axial slot within that in a sleeve. The proximal bearing is arranged to slide distally and proximally about the inner sleeve and radially adjacent the axial slot in the inner sleeve when the elongated lever interface arm is pivoted proximally and distally with respect to that inner sleeve.

When the trigger lever is in its fully opened configuration, the first bifurcated finger arrangement is in its proximalmost orientation. At the same time, the proximal bearing is at its forward or distalmost orientation. That means that the proximal bearing is now radially disposed adjacent and over the axial slot in the inner sleeve. This occurs only when the pivotable lock key has been pivoted downwardly and out of the way, so that the proximal bearing may slide distally over that axial slot.

When the pivotable locked key is pushed downwardly into the bore of the inner sleeve, with the proximal bearing covering the axial slot, the pivotable lock key cannot be pivoted radially outwardly from the bore of that inner sleeve. The pivotable lock key, as aforementioned, has an enlarged distalmost end, which end, in effect, prevents insertion of clip cartridges within the bore of the inner sleeve, thus effecting the prevention of inadvertent loading of subsequent clips until the clip applying device is empty and ready for such further clip loading.

When the trigger lever is pulled towards the fixed handle portion of the pistol shaped housing, the forward bifurcated finger arrangement pushes the distal bearing distally or forward, so as to actuate the jaw pinching mechanism. The elongated linkage bar is directed proximally as the elongated ratchet plate is pivoted about the first trigger axis. As the pivot axis in the elongated lever interface arm and the elongated linkage bar engage, the elongated lever interface arm is caused to pivot rearwardly. The rearward pivoting of the elongated lever interface arm effects rearward or proximal motion of the second bifurcated finger, thus moving the proximal bearing rearwardly about the inner sleeve. Displacement of the proximal bearing rearwardly exposes the axial slot in the inner sleeve, thus permitting the pivotable lock key to be pushed upwardly as a new cartridge is placed or pushed into the proximal end of the inner sleeve to load the clip device into the barrel.

The inner sleeve and its distalmost mechanism is permitted to rotate about its longitudinal axis. The proximal bearing being comprised of an annular ring covers the axial slot in the inner sleeve no matter which orientation the axial slot resides.

Thus what has been shown is a unique safety mechanism for a medical clip applying device permits access to and prevents access to the inner bore of the inner sleeve by a cartridge, thus preventing misuse of the medical clip applying device. The circumferential arrangement of the proximal bearing allows the sleeve to be rotated in any angular position while still effecting the safety lock mechanism.

Thus the invention comprises an elongated medical clip applying device having a hand holdable housing at a proximal end thereof and a barrel clip-dispenser at a distal end thereof for dispensing squeezable clips onto a mammalian tissue. The device includes a hollow inner sleeve arranged within the housing, the sleeve having a proximal end for receiving a clip feeder cartridge therein. A proximal bearing is slidably disposed about a proximal circumference of the inner sleeve. A trigger lever is attached to the housing, the trigger lever having a linkage bat thereon connected to a finger for moving the proximal bearing proximally and distally. A lock mechanism is arranged in the sleeve arranged to deny a clip feeder cartridge entry into the sleeve when the proximal bearing is adjacent the lock mechanism. The lock mechanism may comprise a pivotable key for blocking the hollow inner sleeve. The inner sleeve has an elongated slot therein which slot is arranged to receive the key so as to deny entry and receipt of the clip cartridge in the inner sleeve. The proximal bearing may enclose the entire circumference of a portion of the inner sleeve. The key may have an enlarged distalmost end for effecting the blocking of the inner sleeve. The key may have a proximal end which is pivotally connected by a pivot axis, to the inner sleeve. The finger may be bifurcated to engage the proximal bearing at two sides thereof.

The invention may also comprise a method of locking an elongated medical clip applying device to prevent inadvertent loading of a clip cartridge into an inner sleeve thereof, which sleeve and an extended distal barrel are supportively arranged in a housing of the device It comprises arranging a locking mechanism in a proximal portion of the sleeve in the housing; pulling a trigger lever on the housing to unlock the locking mechanism upon emptying of clips from a cartridge previously loaded into the sleeve and barrel; loading a clip cartridge into a proximal end of the sleeve; and releasing the trigger lever to advance the clip cartridge within the sleeve and barrel of the device. The method includes forming a slot in the inner sleeve at the proximal end thereof, for receipt of the locking mechanism; placing a pivotable key in the slot to effect passage of a clip cartridge within the sleeve; moving a bearing radially adjacent the key in the slot to prevent pivoting of the key from the slot and thereby effectively blocking the sleeve from further loading; moving the bearing from a position radially adjacent the slot and the key, to permit the key to be pivoted outwardly from the slot thereby permitting entry and passage of a clip cartridge therewithin.

BRIEF DESCRIPTION OF THE DRAWINGS

The objects and advantages of the present invention will become more apparent, when viewed in conjunction with the following drawings, in which.

DETAILED DESCRIPTION OF THE PREFERRED EMBODIMENTS

Figure 1:
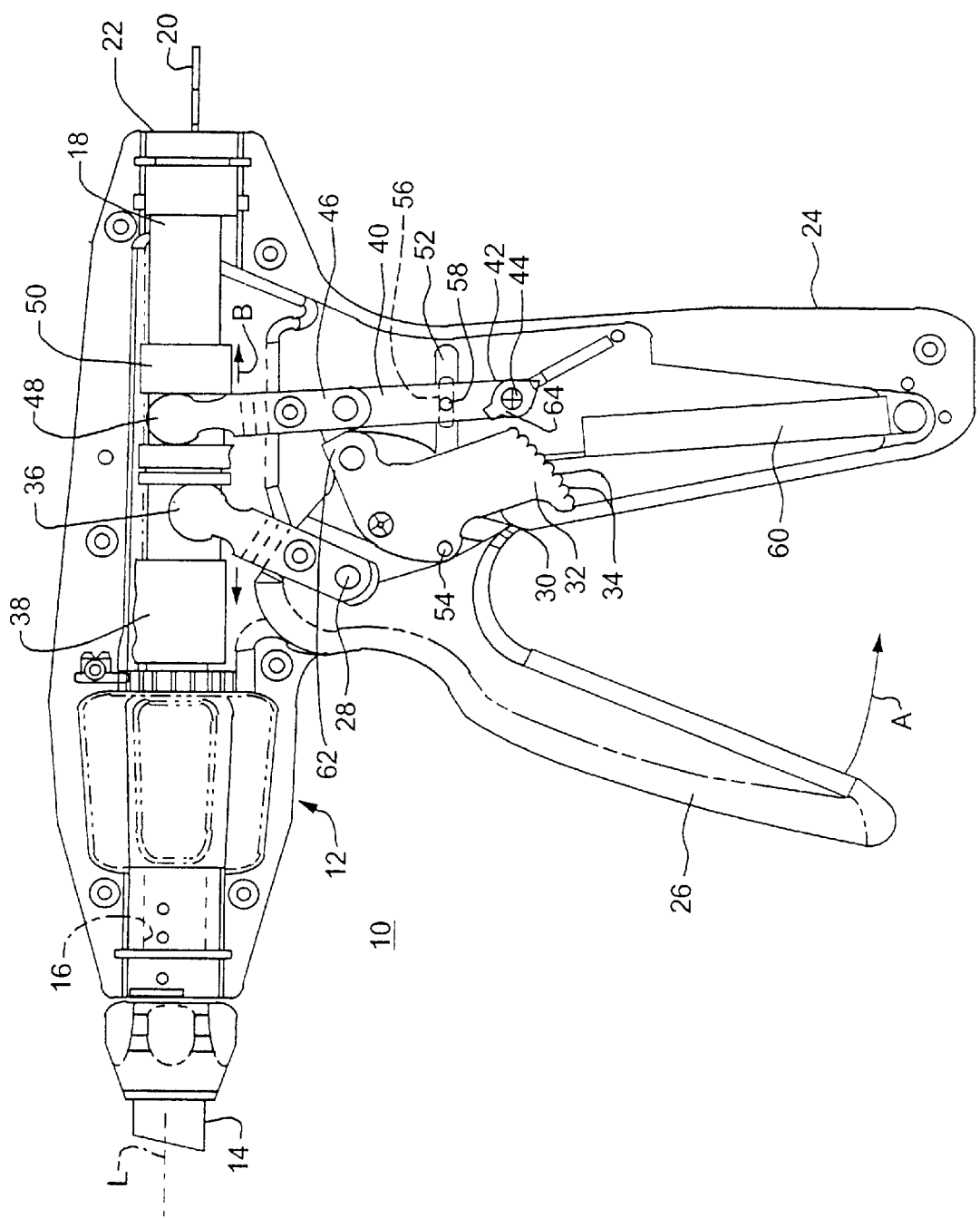
FIG. 1 is a side elevational view of the pistol shaped housing portion of the medical clip applying device of the present invention in a trigger released configuration.

Referring now to the drawings in detail, and particularly to FIG. 1, there is shown the present invention which comprises a a clip applying apparatus 10 utilized in medical procedures for pinching off and clinching together mammalian tissue. Such a clip applying device comprises a pistol shaped housing 12 at a proximal end thereof, with an elongated barrel 14 extending therefrom, the barrel 14 having a distal end from which extends a pair of pincher jaws, not shown for clarity. The pistol-shaped housing 12 has a bore 16 extending therethrough for receipt of an inner sleeve 18. The inner sleeve 18 extends through the housing 12 and itself receives a clip loaded cartridge 20 from its proximalmost end 22.

The housing 12 has a fixed handle portion 24 extending downwardly therefrom. A trigger lever 26 is pivotably disposed in the housing 12 and swings (as shown by arrow "A") about an axis 28 therebetween. An elongated ratchet plate 30 is fixedly attached to the trigger lever 26. The elongated ratchet plate 30 has a distal end 32 with a plurality of ratchet teeth 34 formed thereon.

Figure 2:
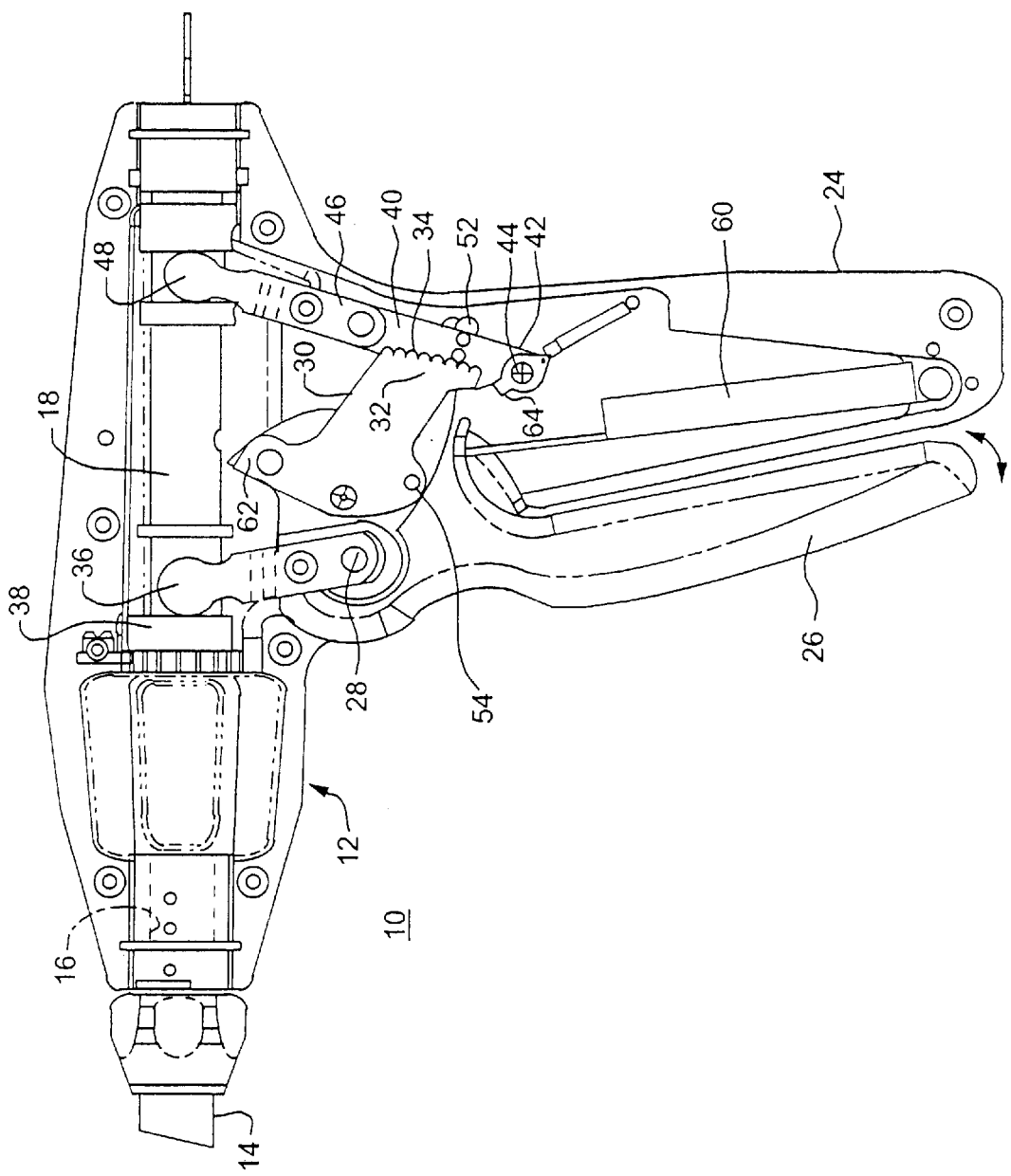
FIG. 2 is a view similar to that of FIG. 1 with the trigger in a pulled or closed configuration.

A first bifurcated finger 36 is fixedly attached to an upper end of the trigger lever 26, and is disposed within the housing 12 about opposite sides of the inner sleeve 18, as may be seen in FIGS. 1 and 2. The first bifurcated finger 36 is disposed about a cylindrical portion of a distal bearing 38 which slides forwardly and rearwardly about the inner sleeve 18. The distal bearing 38 is connected via an elongated shaft, not shown for clarity, to a jaw housing, also not shown for clarity, to effect the motion necessary in the jaw housing to squeeze the pincher jaws closed.

An elongated lever interface arm 40 is arranged within the housing 12, has a lower end 42 which is pivotably attached to a pivot axis 44 attached to the fixed handle 24 of the housing 12 at a midpoint thereof, as may be seen in FIGS. 1 and 2. The elongated lever interface 40 arm has a distal end 46 comprised of a second bifurcated finger 48 which is disposed about opposite sides of a proximal bearing 50. The proximal bearing 50 is disposed on the proximal end of the inner sleeve 18 within the pistol shaped housing 12.

An elongated linkage bar 52 is pivotably attached at a first end thereof, to a pivot axis 54 in the trigger lever 26 and the elongated ratchet plate 30. The linkage bar 52 has an elongated slot 56 disposed therein in an axial arrangement near its second or distal end. A slot pivot pin 58 extends through a pivot hole in the elongated lever interface arm 40 and into the axially directed slot 56 near the distal end of the linkage bar 52.

A coiled spring 60 is arranged between the lowermost end of the fixed handle 24 and an extension 62 arranged on the upper end of the elongated ratchet plate 30. The coiled spring 60 provides a biasing force against which the trigger lever 26 must be pulled.

A ratchet pawl 64 is arranged around the pivot axis 44 on the lowermost or proximal end 42 of the elongated lever interface arm 40. The ratchet pawl 64 is arranged to engage the ratchet teeth 34 on the distal end 32 of the elongated ratchet plate 30.

Figure 3:
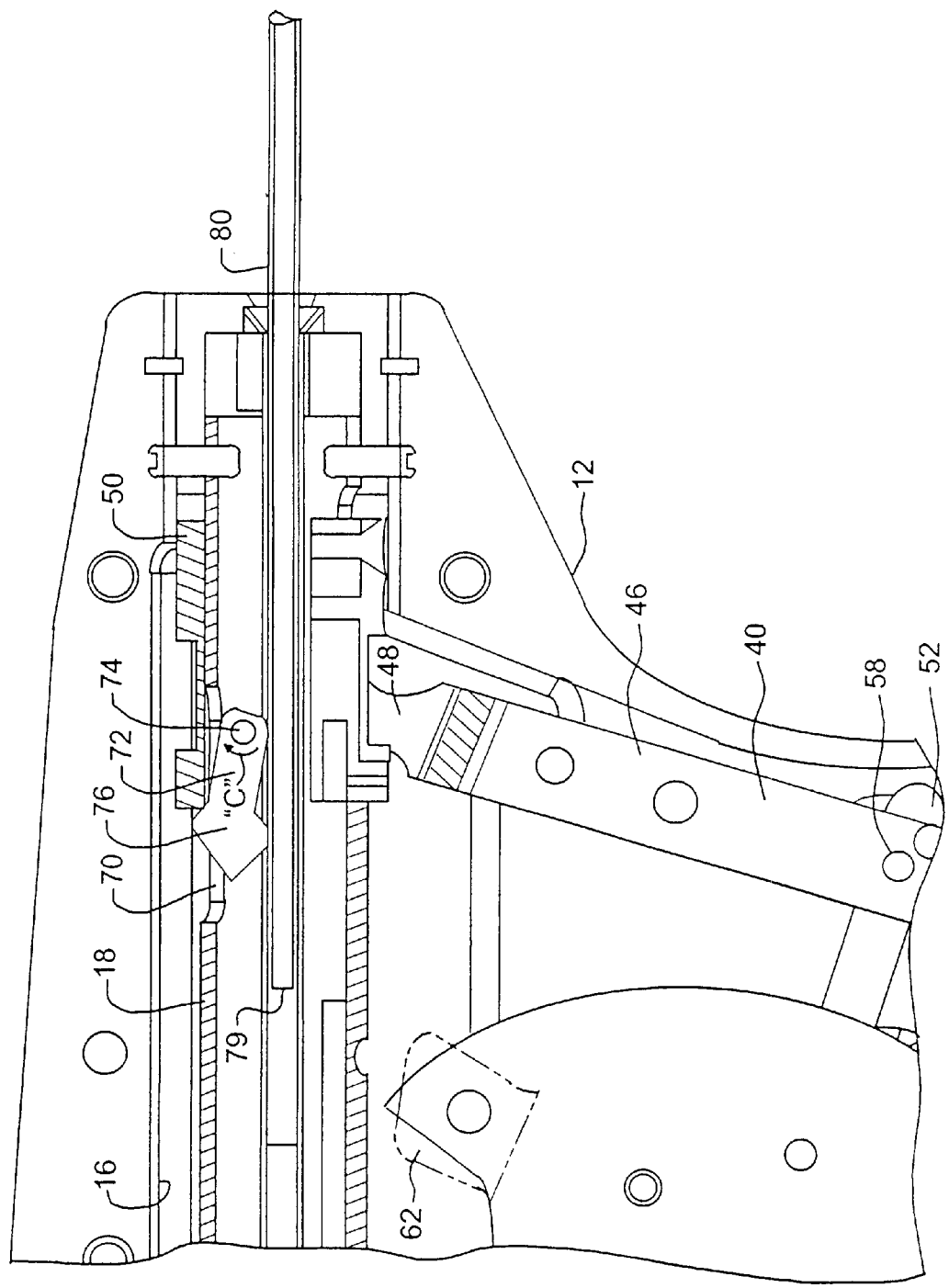
FIG. 3 is a side elevational view, partly in section of the safety locking mechanism of the present invention in an opened position.
Figure 4:
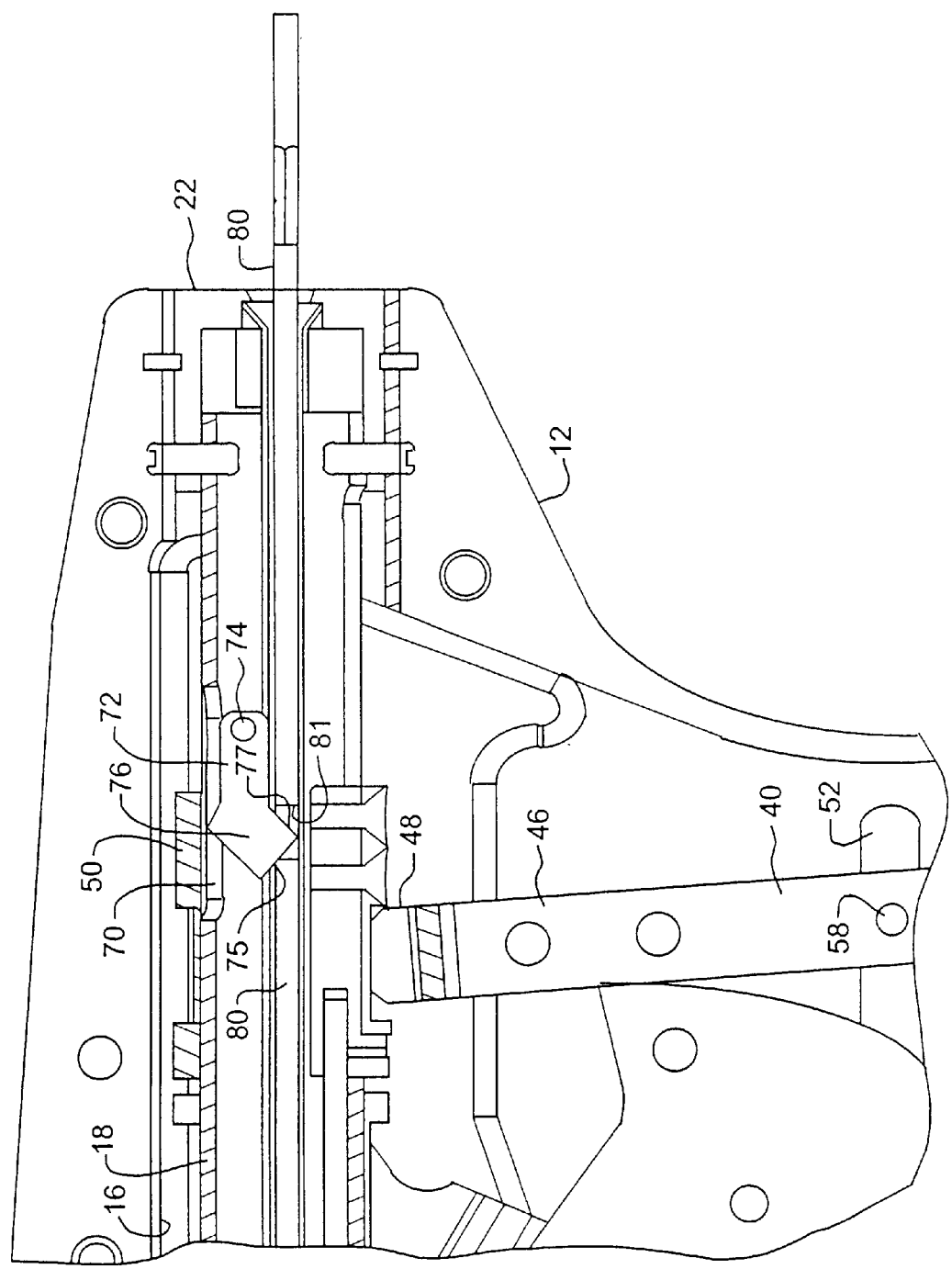
FIG. 4 is a view similar to FIG. 3 with the safety locking mechanism in a closed or safety orientation.

The inner sleeve 18 arranged within the bore 16 of the pistol shaped housing 12 has an elongated slot 70 arranged in an axially disposed orientation at a midpoint thereof, as may be seen in FIGS. 3 and 4. An elongated lock key 72 is pivotably disposed within the inner sleeve 18 in the housing 12, about a key pivot axis 74, which axis 74 is fixed within the inner sleeve cylinder 18. The pivotable lock key 72 has an enlarged distalmost end 76 which is arranged to pivot into and out of the bore of the inner sleeve 18, and within the axial slot 70 within that in a sleeve 18, as may be seen in the relationship of FIGS. 3 and 4. The proximal bearing 50 is arranged to slide distally and proximally about the inner sleeve 18 and radially adjacent the axial slot 72 in the inner sleeve 18 when the elongated lever interface arm 40 is pivoted proximally and distally with respect to that inner sleeve 18.

When the trigger lever 26 is in its fully opened configuration as shown in FIG. 1, the first bifurcated finger 36 is in its proximalmost orientation. At the same time, the proximal bearing 50 is at its forward or distalmost orientation, as also may be seen in FIGS. 1 and 4. That means that the proximal bearing 50 is now radially disposed adjacent and over the axial slot 70 in the inner sleeve 18 as is clearly represented in FIG. 4. This occurs only when the pivotable lock key 72 has been pivoted downwardly and out of the way, so that the proximal bearing 50 may slide distally over that axial slot 70, as shown in FIG. 4.

When the pivotable locked key is pushed slightly downwardly into the bore of the inner sleeve 18, with the proximal bearing 50 covering the axial slot 70, the pivotable lock key 72 cannot be pivoted radially outwardly from the bore of that inner sleeve 18. The pivotable lock key 72, as aforementioned, has an enlarged distalmost end 76, with a pair of cam edges 75 and 77, which enlarged end 76, in effect, prevents insertion of clip cartridges 80 into the bore of the inner sleeve 18, shown as being blocked in FIG. 4, by wedging against a forward end 79 of the clip cartridge 80, thus effecting the prevention of inadvertent loading of subsequent clip cartridges 80 until the clip applying device 10 is empty and ready for such further clip loading. A hole 81 in the clip cartridge 80 is engaged by the cam edges 75 and 77 to lock that cartridge 80 in place as shown in FIG. 4. This establishes the clip applying apparatus 10 as being fully loaded. Once this has occurred, the proximal bearing 50 may then be allowed to be moved distally.

When the trigger lever 26 is pulled towards the fixed handle portion 24 of the pistol shaped housing 12 as shown in FIG. 2, the forward bifurcated finger 36 pushes the distal bearing 38 distally or forward, so as to actuate the jaw pinching mechanism, not shown. The elongated linkage bar 52 is directed proximally as the elongated ratchet plate 30 is pivoted about the first trigger axis 54. As the pivot axis 58 in the elongated lever interface arm 40 and the elongated linkage bar 52 engage, the elongated lever interface arm 40 is caused to pivot rearwardly, as indicated by arrow "B". The rearward pivoting of the elongated lever interface arm 40 effects rearward or proximal motion of the second bifurcated finger 48, thus moving the proximal bearing 50 rearwardly about the inner sleeve 18. Displacement of the proximal bearing 50 rearwardly exposes the axial slot 70 in the inner sleeve 18, thus permitting the pivotable lock key 72 to be pushed upwardly, as indicated by arrow "C" in FIG. 3, as a new clip cartridge 80 is placed or pushed into the proximal end 22 of the inner sleeve 18 to load clip into the barrel 14. inner bore of the inner sleeve by a cartridge, thus preventing misuse of the medical clip applying device. The circumferential arrangement of the proximal bearing allows the sleeve to be rotated in any angular position while still effecting the safety lock mechanism.

We claim:

1. An elongated medical clip applying device having a hand holdable housing at a proximal end thereof and a barrel clip-dispenser at a distal end thereof for dispensing squeezable clips onto a mammalian tissue, said device including
    a hollow inner sleeve arranged within said housing, said sleeve having a proximal end for receiving a clip feeder cartridge therein;
    a proximal bearing slidably disposed about a proximal circumference of said inner sleeve;
    a trigger lever attached to said housing, said trigger lever having a linkage bar thereon connected to a finger for moving said proximal bearing proximally and distally; and
    a lock mechanism arranged in said sleeve arranged to deny a clip feeder cartridge entry into said sleeve when said proximal bearing is adjacent said lock mechanism.

2. The elongated medical clip applying device as recited in claim 1, wherein said lock mechanism comprises a pivotable key for blocking said hollow inner sleeve.

3. The elongated medical clip applying device as recited in claim 2, wherein said inner sleeve has an elongated slot therein which slot is arranged to receive said key so as to deny entry and receipt of said clip cartridge in said inner sleeve.

4. The elongated medical clip applying device as recited in claim 2, wherein said proximal bearing encloses the entire circumference of a portion of said inner sleeve.

5. The elongated medical clip applying device as recited in claim 2, wherein said key has an enlarged distalmost end for effecting said blocking of said inner sleeve.

6. The elongated medical clip applying device as recited in claim 2, wherein said key has a proximal end which is pivotally connected by a pivot axis, to said inner sleeve.

7. The elongated medical clip applying device as recited in claim 2, wherein said finger is bifurcated to engage said proximal bearing at two sides thereof.

8. The elongated medical clip applying device as recited in claim 5, wherein said enlarged distalmost end of said key has a cam edge thereon for locking engagement with said clip cartridge.

9. A method of locking an elongated medical clip applying device to prevent inadvertent loading of a clip cartridge into an inner sleeve thereof, which sleeve and an extended distal barrel supportively arranged in a housing of said device, comprising:
    arranging a locking mechanism in a proximal portion of said sleeve in said housing;
    pulling a trigger lever on said housing to unlock said locking mechanism upon emptying of clips from a cartridge previously loaded into said sleeve and barrel;
    loading a clip cartridge into a proximal end of said sleeve; and
    releasing said trigger lever to advance said clip cartridge within said sleeve and barrel of said device.

10. The method as recited in claim 9, including:
    forming a slot in said inner sleeve at said proximal end thereof, for receipt of said locking mechanism.

11. The method as recited in claim 10, including:

placing a pivotable key in said slot to effect passage of a clip cartridge within said sleeve.

12. The method as recited in claim 11, including:

moving a bearing radially adjacent said key in said slot to prevent pivoting of said key from said slot and thereby effectively blocking said sleeve from further loading.

13. The method as recited in claim 12, including:

moving said bearing from a position radially adjacent said slot and said key, to permit said key to be pivoted outwardly from said slot thereby permitting entry and passage of a clip cartridge therewithin.

14. The method as recited in claim 12, including:

pivoting said locking mechanism into engagement with a hole in said clip cartridge to lock said cartridge in said clip applying device.

\* \* \* \* \*